United States Patent [19]
Meunier et al.

[11] Patent Number: 6,077,860
[45] Date of Patent: Jun. 20, 2000

[54] INSECTICIDAL COMBINATIONS INCLUDING AN INSECTICIDE FROM THE CHLORONICOTINYL FAMILY AND AN INSECTICIDE HAVING A PYRAZOLE, PYRROLE OR PHENYLIMIDAZOLE GROUP

[75] Inventors: Lucien Meunier, Yamoussokro, South Africa; Pascal Caruhel, Meyzieu; Francis Molle, Villeurbanne, both of France

[73] Assignee: Rhone-Poulenc Agrochimie, Lyon, France

[21] Appl. No.: 09/318,813

[22] Filed: May 26, 1999

Related U.S. Application Data

[62] Division of application No. 08/875,621, Oct. 22, 1997, Pat. No. 5,952,358.

[30] Foreign Application Priority Data

Jan. 30, 1995 [FR] France .................................. 95 01300
May 4, 1995 [FR] France .................................. 95 05542

[51] Int. Cl.$^7$ ............................ A01N 43/40; A01N 43/56
[52] U.S. Cl. ............................................ 514/341; 514/404
[58] Field of Search ..................... 514/404, 341

[56] References Cited

U.S. PATENT DOCUMENTS 5,232,940  8/1993  Hatton et al. ........................... 514/407

FOREIGN PATENT DOCUMENTS

| | | |
|---|---|---|
| 0295117 | 12/1988 | European Pat. Off. . |
| 0460940 | 12/1991 | European Pat. Off. . |
| 0484165 | 5/1992 | European Pat. Off. . |
| 91/04965 | 4/1991 | WIPO . |
| 93/24004 | 12/1993 | WIPO . |
| 96/03879 | 2/1996 | WIPO . |
| 96/37105 | 11/1996 | WIPO . |
| 97/24032 | 7/1997 | WIPO . |

OTHER PUBLICATIONS

Colliot et al, Brighton Crop Protection Conference–Pests and Diseases–1992, 2–1, pp. 29–34.
Elbert et al, Brighton Crop Protection Conference–Pests and Diseases–1990, 2–1, pp. 21–28.
*The Pesticide Manual*, tenth edition, ed. Clive Tomlin, British Crop Protection Council and The Royal Society of England, United Kingdom, 1994, pp. 463, 591–593, 730, 736–737.

*Primary Examiner*—Allen J. Robinson
*Attorney, Agent, or Firm*—Burns, Doanne, Swecker & Mathis, L.L.P.

[57] ABSTRACT

Agrochemical combinations including an effective amount of an insecticide which includes an insecticide from the chloronicotinyl family A such as imidacloprid, acetamiprid or nitenpyram, and an insecticide B having a pyrazole, pyrrole or phenylimidazole group; compositions containing one or both of said two active substances; and a method for treating and protecting plants, and seeds in particular, from insects or arthropods, by applying a combination of both active substances, are disclosed. A composition containing both active substances may also be applied. Alternatively, two compositions each containing one of the active substances may be applied simultaneously or sequentially to ensure a combined effect.

38 Claims, No Drawings

INSECTICIDAL COMBINATIONS INCLUDING AN INSECTICIDE FROM THE CHLORONICOTINYL FAMILY AND AN INSECTICIDE HAVING A PYRAZOLE, PYRROLE OR PHENYLIMIDAZOLE GROUP

CROSS-REFERENCE TO RELATED APPLICATIONS

This application is a divisional of application Ser. No. 08/875,621, filed Oct. 22, 1997, now U.S. Pat. No. 5,952,358, which is the U.S. national phase of International Patent Application No. PCT/FR96/00132, filed Jan. 26, 1996, and which is incorporated by reference herein in its entirety and relied upon.

The present invention relates to novel agrochemical combinations, for the protection of plants, comprising at least one effective quantity of an insecticide A from the class of the chloronicotinyls, such as imidacloprid, acetamiprid or nitenpyram, and at least one effective quantity of an insecticide B other than an organophosphorus, pyrethroid or carbamate insecticide, and to a method for treating plants using these combinations.

In the context of the present invention, the term plant refers to an entire plant, a part of the plant or the propagation material of the plant, especially the seed.

More advantageously, the subject of the invention is an agrochemical combination for the protection of plants against insects or arthropods, characterized in that an effective quantity of an insecticide comprising an insecticide A from the class of the chloronicotinyl, such as imidacloprid, acetamiprid or nitenpyram, and an insecticide B with a pyrazole, pyrrole or phenylimidazole group, is used.

Insecticides B with a pyrazole, pyrrole or phenylimidazole group include those described in the applications for European Patents EP 0295117, EP 0460940 or EP 0484165, respectively. Preferably, the insecticide chosen in the present invention is from the class of insecticides with a pyrazole group. Advantageously, the compound chosen is that whose common name is fipronil, of chemical formula (±)-5-amino-1-(2,6-dichloro-α, α,α-trifluoro-p-tolyl)-4-trifluoromethylsulphinylpyrazole-3-carbonitrile, the compound 5-amino-1-(2,6-dichloro-α,α,α-trifluoro-p-tolyl)-4-ethylsulphinylpyrazole-3-carbonitrile or the compound 5-methylamino-1-(2,6-dichloro-α,α,α-trifluoro-p-tolyl)-4-ethylsulphinylpyrazole-3-carbonitrile. Apart from its disclosure in the application EP 0295117, the properties of the compound fipronil have been published in the report of the 1992 Brighton Crop Protection Conference (Pests and Diseases, pages 29–34).

Imidacloprid is the common name for 1-(6-chloro-3-pyridylmethyl)-N-nitroimidazolidin-2-ylideneamine, the insecticidal properties of which have been described, in particular in the "Pests and diseases" reports of the 1990 Brighton Crop Protection Conference, p. 21.

Acetamiprid is the common name for (E)-N$^1$-((6-chloro-3-pyridyl) methyl)-N$^2$-cyano-N$^1$-methyl-acetamidine. This product is listed in the Pesticide Manual (tenth edition) under its code number NI-25. It was first disclosed in the international application PCT/JP90/01282 published under the number WO 91/04965. Since then, other properties of this compound have been described in the international application PCT/EP93/01286 published under the number WO 93/24004.

Nitenpyram is the common name for (E)-N-((6-chloro-3-pyridyl) methyl)-N-ethyl-N'-methyl-2-nitrovinylidenediamine. This product is listed in the Pesticide Manual (tenth edition), edited by Clive TOMLIN and published by the British Crop Protection Council, 1994.

Preferably, the combinations according to the invention can be used for the protection of seeds or in treating the soil.

A further subject of the invention is compositions comprising an abovementioned combination according to the invention.

The invention additionally comprises a method for the anti-insect or anti-arthropod treatment of plants, characterized in that a combination of the two active ingredients is applied. It is also possible to apply a composition containing the two active ingredients or, either simultaneously or in succession so as to have the combined effect, two compositions each containing one of the two active ingredients.

A further subject of the invention is a method of treating seeds, characterized in that the said seed is chosen from the group consisting of cereals (e.g. wheat, barley, rye), maize, sorghum, sunflower, cotton, rice, peas, colza, potato and market-garden crops.

The application rates of the combinations of compounds according to the invention can vary within wide limits, in particular according to the type of seed and according to the virulence, nature and extent of attack by the insects or arthropods and the climatic conditions. The insecticide (B), preferably fipronil, is used at a rate ranging from 10 to 500 g, preferably from 40 to 300 g, per quintal (g/q), and the insecticide A, preferably imidacloprid, acetamiprid or nitenpyram, is used at a rate ranging from 10 to 800 g, preferably from 20 to 500 g, per quintal of seed, the ratio B/A then being between 0.0125 and 50, preferably between 0.08 and 15, and the ratio A/B being between 0.02 and 80, preferably between 0.067and 12.5.

In the case of treatment of maize or sorghum seeds, the rates used will be from 20 to 500 g/q for the insecticide A, preferably imidacloprid, acetamiprid or nitenpyram and from 40 to 300 g/q for the insecticide B (preferably fipronil).

Another subject of the present invention is a method of treating beet seeds with the abovementioned compositions or combinations.

In the case of treatment of beet seeds, the rates used will be from 20 to 100 g/unit for the insecticide A, preferably imidacloprid, acetamiprid or nitenpyram, and from 25 to 50 g/unit for the insecticide B (preferably fipronil). The unit is the quantity of seed required to sow one hectare.

In accordance with one variant, a further subject of the invention is a method of treating soil by the application, in particular into the seed drill:

either of a granular formulation containing the two active ingredients in combination or as a composition, or of a mixture of two granular formulations, each containing one of the two active ingredients, with optionally one or more solid or liquid, agriculturally acceptable carriers and/or optionally with one or more agriculturally acceptable surfactants.

This method is advantageously employed in seedbeds of cereal, maize, cotton and sunflower. For cereals and maize, the rates for an insecticide from the class of the chloronicotinyls, such as imidacloprid, acetamiprid or nitenpyram, are between 50 and 500 g/ha (grammes per hectare) and those of the insecticide B (preferably fipronil) are between 50 and 200 g/ha.

The methods according to the invention are particularly useful for the destruction of insect or arthropod pests.

Among these insects, the various varieties of flies, such as the wheat bulb fly (*Phorbia coarctata*) or the seedcorn maggot (*Phorbia platura*), Atomaria, millipedes, centipedes, Cicadellidae, aphids and also click beetles and wireworms (*Agriotes sp., Athous haemorrhoidalis*) are destroyed through the use of a combination, composition and/or treatment according to the invention.

The invention also relates to the propagation product of the plants, and especially the seed, coated with and/or containing a combination as defined above or a composition containing the mixture of two active ingredients or a mixture of two compositions each providing one of the two active ingredients. It will easily be understood that the seed can in particular be treated either with a composition comprising insecticide B, preferably fipronil, then with a composition comprising the insecticide A, preferably imidacloprid, acetamiprid or nitenpyram, or vice versa, or with a composition containing the two active ingredients.

The term "coated with and/or containing" generally signifies that the active ingredient is for the most part on the surface of the propagation product at the time of application, although a greater or lesser part of the ingredient may penetrate into the product, depending on the method of application. When the said propagation product is replanted, it absorbs the active ingredient. In effect, it can be stated for commercial purposes that the majority of the active ingredient is on the surface most of the time.

The invention also relates to a product comprising an insecticide A from the class of the chloronicotinyls, such as imidacloprid, acetamiprid or nitenpyram, A, and an insecticide B with a pyrazole, pyrrole or phenylimidazole group, preferably fipronil, for a simultaneous, successive or sequential application in the protection of plants against insects or arthropods.

The examples which follow are given to illustrate the combinations, compositions and treatment according to the invention. These examples are of course non-limiting, and many other plants can be treated and insects or arthropods controlled by the combinations and compositions according to the invention.

EXAMPLE 1

Maize seeds were treated in accordance with a conventional seed treatment:

on the one hand with a suspension concentrate FS of fipronil at a concentration of 500 g ai/l (0.125 l/q).

on the other hand, with a wettable powder for seed treatment WS of imidacloprid (Gaucho WS) at a concentration of 700 g ai/kg (0.35 or 0.7 kg of this formulation are used per quintal of seed).

finally, one portion is treated with 0.125 l/q of fipronil and 0.35 kg/q of imidacloprid.

An untreated portion of seed serves as control sample. In addition, a comparison is also made with carbofuran, which is applied in the form of microgranules into the seed drill. The maize seeds thus treated, or the control seeds, are planted into virgin soil, while an untreated portion is planted in a plot in which granules of carbofuran are present. 49 days after sowing, an evaluation is made of the percentage of plants which have been attacked by wireworm (*Agriotes sp.*). The results are as follows:

| Treatment | % (plants attacked) |
| --- | --- |
| Untreated control | 90 |
| Fipronil 62.5 g ai/q | 18.3 |
| Fipronil 62.5 g/q + imidacloprid 245 g/q | 3.1 |
| Imidacloprid 245 g ma/q | 20 |
| Imidacloprid 490 g ai/q | 5 |
| Carbofuran 600 g ai/ha | 10 |

This example illustrates well the superiority of the combinations, compositions and methods according to the, invention relative both to the insecticides alone and to a commercial reference product.

Moreover, no phytotoxicity phenomenon is observed in this example.

EXAMPLE 2

Trial on Barley (*Rhopalosiphum padi*). Imidacloprid+Fipronil

Barley seeds were treated as follows:

a) one part with 50 g/q of fipronil, b) one part with 35 g/q of imidacloprid, c) one part with 50 g/q of fipronil +35 g/q of imidacloprid, d) finally, a last quantity of seeds is not treated and serves as control.

160 days after having sown the barley seeds, an analysis of the percentage discoloration associated with infection by barley yellow dwarf virus transmitted by *Rhopalosiphum padi* shows that there is 6.3% discoloration in the case of c) as against 67.8 and 19.5% respectively in the cases a) and b). The control plants d) are discoloured by more than 80% (81.3%). It is noted that the two insecticides individually make it possible to reduce the discoloration but that this reduction is markedly more pronounced when the two products are combined.

EXAMPLE 3

Trial on *Plutella xylostella*. Acetamiprid+Fipronil

The trial carried out on the diamondback moth (*Plutella xylostella*) showed that the addition of an ineffective quantity of NI25 (acetamiprid) to fipronil made it possible to reduce the dose of the latter by a factor of 2.5 (synergy ratio) to obtain the same activity.

The test is carried out as follows: *Plutella xylostella* larvae at an intermediate stage in their development (3rd larval stage) are placed on cabbage leaves which serve as biological support. Different leaves are then treated with varying concentrations of active ingredient and, 48 h after treatment, the dead larvae are counted. From the mortality curve as a function of the concentration of active ingredient, the LC50 (concentration which destroys 50% of the population) is determined. The lethal concentration 50 is obtained with 0.4 ppm of fipronil on its own. The LC50 of NI25 is 40 ppm. When a mixture of fipronil (2 doses)+NI25 (1 dose) is used, the LC50 becomes 0.16 ppm (dose expressed in concentration of fipronil).

EXAMPLE 4

Trial on Aubergine (*Myzus persicae*) Acetamiprid +Fipronil

A certain number of aubergine plants are infested with the green peach aphid (*Myzus persicae*). A number of untreated plants serve as control and make it possible to calculate the percentage activity obtained on plants treated beforehand either with fipronil on its own, in various doses, or with acetamiprid on its own, or, finally, with the tank mix. The percentage mortality of the insect is read off 3 days after foliar treatment of the aubergine plants, and this readoff leads to the results set out in the following table:

| fipronil\NI25 | 0 g/ha | 6.25 g/ha | Expected result E** | Synergy |
|---|---|---|---|---|
| 0 g/ha | 0%* | 2% | — | — |
| 3.13 g/ha | 0% | 6% | 2% | +4% |
| 12.5 g/ha | 0% | 47% | 2% | +45% |
| 50 g/ha | 23% | 72% | 20.4% | +51.6% |

*Untreated control.
**As calculated by the Colby formula, which is well known to the skilled worker:
$E = X + Y - X.Y/100$ in which:
E is the expected percentage of insect mortality for a mixture of two insecticides A and B at defined doses, equal to a and b respectively, X is the observed percentage mortality for the insecticide A at the dose a, and Y is the observed percentage mortality for the insecticide B at the dose b. When the percentage mortality obtained for the mixture is greater than E, there is synergy.

For their use in practice, the combinations according to the invention are rarely employed alone and can be employed in compositions containing one or other of the active ingredients or else both together. In each composition, the active ingredients are customarily combined with an agriculturally utilizable, liquid or solid carrier and, optionally, with at least one surfactant.

These compositions, which can be used for the protection of plants against insects, contain as active ingredient at least one of the constituents of the combination according to the invention as described above in combination with agriculturally acceptable, liquid or solid carriers and/or agriculturally acceptable surfactants. It is possible in particular to use the customary inert carriers and the customary surfactants.

These compositions customarily contain between 0.5 and 95% of compound according to the invention, i.e. either of the combination or of one of the two active ingredients. Unless otherwise stated, in this description the percentages are expressed by weight.

The term "carrier" in the present description denotes a natural or synthetic, inorganic or organic substance with which the active ingredient is combined to facilitate its application to the plant, to seeds or to the soil. This carrier is therefore generally inert and must be agriculturally acceptable, especially on the plant treated. The carrier can be solid (clays, natural or synthetic silicates, silica, resins, waxes, solid fertilizers, etc.) or liquid (water, alcohols, ketones, petroleum fractions, aromatic or paraffinic hydrocarbons, chlorinated hydrocarbons, liquefied gases, etc.).

The surfactant can be an emulsifier, dispersant or wetting agent of ionic or nonionic type. Examples which may be mentioned are salts of polyacrylic acids, salts of lignosulphonic acids, salts of phenylsulphonic or naphthalenesulphonic acids, polycondensates of ethylene oxide with fatty alcohols or with fatty acids or with fatty amines, substituted phenols (especially alkylphenols or arylphenols), sulphosuccinic ester salts, taurine derivatives (especially alkyltaurates), or phosphoric esters of polyethoxylated phenols or alcohols. The presence of at least one surfactant is generally essential when the active ingredient and/or the inert carrier are insoluble in water and the vehicle for the application is water.

These compositions can also contain any kind of other ingredients, such as, for example, protective colloids, adhesives, thickeners, thixotropic agents, penetration agents, stabilizers, sequestrants, etc., and also other active ingredients known for their pesticidal (especially insecticidal or fungicidal) properties or their plant growth-promoting properties (especially fertilizers) or their plant growth-regulating properties. More generally, the compounds according to the invention can be combined with all of the solid or liquid additives which correspond to the customary techniques of formulation.

For their application, the constituents of the combination are therefore often in the form of compositions which are themselves in relatively diverse, solid or liquid forms.

Compositions in solid form which may be mentioned are powders for dusting or dispersion (with a content of combination according to the invention which may range up to 100%) and granules, especially those obtained by extrusion, by compacting, by impregnation of a granular support or by granulation from a powder (the content of combination according to the invention in these granules being between 0.5% and 80% in the latter cases).

In an example of the composition of granules, the following constituents are used:

EXAMPLE G

| | |
|---|---|
| - combination or one of the two active ingredients | 50 g |
| - epichlorohydrin | 2.5 g |
| - cetyl polyglycol ether | 2.5 g |
| - polyethylene glycol | 35 g |
| - kaolin (particle size: 0.3 to 0.8 mm) | 910 g |

In this particular case, the active ingredients are mixed with epichlorohydrin and the mixture is dissolved with 60 g of acetone, then the polyethylene glycol and the cetyl polyglycol ether are added. The kaolin is soaked with the solution obtained and then the acetone is evaporated off under vacuum.

The compounds or combinations of the said compounds can also be used in the form of powders for dusting. It is also possible to use a composition containing 50 g of active ingredient(s) and 950 g of talc or else to use a composition containing 20 g of active ingredient(s), 10 g of finely divided silica and 970 g of talc. These constituents are mixed and ground and the mixture is applied by dusting.

Compositions which may be mentioned and which are in liquid form or which are intended to constitute liquid compositions at the time of application include solutions, especially water-soluble concentrates, emulsifiable concentrates, emulsions, suspension concentrates, aerosols, wettable powders and pastes.

The emulsifiable or soluble concentrates usually comprise from 10 to 80% of active ingredient, whereas the ready-to-apply solutions or emulsions contain from 0.01 to 20% of active ingredient.

For example, in addition to the solvent, the emulsifiable concentrates may contain, where necessary, from 2 to 20% of appropriate additives, such as the abovementioned stabilizers, surfactants, penetration agents, corrosion inhibitors, dyes or adhesives.

The suspension concentrates which can also be applied by spraying are prepared so as to obtain a stable fluid product which does not form deposits, and they customarily contain from 2 to 75% of active ingredient, from 0.5 to 15% of surfactants, from 0.1 to 10% of thixotropic agents, from 0 to 10% of appropriate additives, such as antifoams, corrosion inhibitors, stabilizers, penetration agents and adhesives, and, as carrier, water or an organic liquid in which the active ingredient is of low or zero solubility. Certain solid organic substances or inorganic salts may be dissolved in the carrier to help prevent sedimentation, or as antifreeze agents for the water.

An example of such a formulation is given below:

EXAMPLE SC

| - active ingredient | 600 g |
|---|---|
| - polyethoxylated tristyrylphenol phosphate | 50 g |
| - polyethoxylated alkylphenol | 50 g |
| - sodium polycarboxylate | 20 g |
| - ethylene glycol | 50 g |
| - organopolysiloxane oil (antifoam) | 1 g |
| - polysaccharide | 1.5 g |
| - water | qs 1 l |

The wettable powders are customarily prepared such that they contain from 20 to 95% of active ingredient, and they usually contain, in addition to the solid carrier, from 0 to 5% of a wetting agent, from 3 to 10% of a dispersant and, where necessary, from 0 to 10% of one or more stabilizers and/or other additives, such as penetration agents, adhesives, anti-caking agents, dyes, etc.

In order to obtain these wettable powders, the active ingredients are intimately mixed in appropriate mixers with the additional substances, and the mixtures are ground with appropriate mills or other grinders. In this way, wettable powders are obtained whose wettability and suspension characteristics are advantageous. They can be suspended with water at any concentration desired.

In place of wettable powders it is possible to form pastes. The conditions and methods for the production and use of these pastes are similar to those for the wettable powders.

As already mentioned, the aqueous emulsions and dispersions, for example the compositions obtained by diluting a wettable powder or an emulsifiable concentrate according to the invention with water, are included within the general scope of the present invention. The emulsions can be of the water-in-oil or oil-in-water type and may have a thick consistency like that of a mayonnaise sauce.

What is claimed is:

1. An agrochemical combination comprising a synergistic arthropodicidally effective amount of imidacloprid and fipronil, the ratio by weight of imidacloprid to fipronil being between 0.02 and 80.

2. A combination according to claim 1, wherein the arthropodicidally effective amount is an insecticidally effective amount.

3. A combination according to claim 1, wherein the ratio by weight of imidacloprid to fipronil is between 0.067 and 12.5.

4. An agrochemical composition comprising:
   (a) a synergistic arthropodicidally effective amount of imidacloprid and fipronil, the ratio by weight of imidacloprid to fipronil being between 0.02 and 80; and
   (b) at least one member selected from the group consisting of an agriculturally acceptable solid or liquid carrier and an agriculturally acceptable surfactant.

5. A composition according to claim 4, wherein the arthropodicidally effective amount is an insecticidally effective amount.

6. A composition according to claim 4, wherein the ratio by weight of imidacloprid to fipronil is between 0.067 and 12.5.

7. A composition according to claim 4, comprising between 0.5% and 95% of the active ingredients imidacloprid and fipronil.

8. A method for the protection of plants against arthropods, said method comprising applying to said plants or their seed or to the locus in which they grow a synergistic arthropodicidally effective amount of imidacloprid and fipronil, the ratio by weight of imidacloprid to fipronil being between 0.02 and 80.

9. A method according to claim 8 for the protection of plants against insects, wherein the synergistic arthropodicidally effective amount is a synergistic insecticidally effective amount.

10. A method according to claim 8, wherein the ratio by weight of imidacloprid to fipronil is between 0.067 and 12.5.

11. A method according to claim 8, wherein the active ingredients imidacloprid and fipronil are applied in the form of an agrochemical composition comprising:
   (a) a synergistic arthropodicidally effective amount of imidacloprid and fipronil, the ratio by weight of imidacloprid to fipronil being between 0.02 and 80; and
   (b) at least one member selected from the group consisting of an agriculturally acceptable solid or liquid carrier and an agriculturally acceptable surfactant.

12. A method according to claim 11 for the protection of plants against insects, wherein the synergistic arthropodicidally effective amount is a synergistic insecticidally effective amount.

13. A method according to claim 11, wherein the ratio by weight of imidacloprid to fipronil is between 0.067 and 12.5.

14. A method according to claim 8, wherein the active ingredients imidacloprid and fipronil are applied to plant seed.

15. A method according to claim 14, wherein the plant seed is cereal, maize, sorghum, sunflower, cotton, rice, pea, colza, potato or market-garden crop seed.

16. A method according to claim 15, wherein the cereal seed is wheat, barley or rye seed.

17. A method according to claim 15, wherein imidacloprid is applied at a rate of from 10 to 800 grams per quintal of seed and fipronil is applied at a rate of from 10 to 500 grams per quintal of seed.

18. A method according to claim 17, wherein the plant seed is maize seed or sorghum seed, and wherein imidacloprid is applied at a rate of from 20 to 500 grams per quintal of seed, and fipronil is applied at a rate of from 40 to 300 grams per quintal of seed.

19. A method according to claim 14, wherein the plant seed is beet seed.

20. A method according to claim 19, wherein imidacloprid is applied at a rate of from 20 to 100 grams per unit and fipronil is applied at a rate of from 25 to 50 grams per unit, said unit being the quantity of seed required to sow one hectare.

21. A method according to claim 8, wherein the active ingredients imidacloprid and fipronil are applied simultaneously.

22. A method according to claim 8, wherein the active ingredients imidacloprid and fipronil are applied in succession so as to afford a combined synergistic arthropodicidal effect.

23. A method according to claim 22, wherein the active ingredient imidacloprid is applied prior to the active ingredient fipronil.

24. A method according to claim 22, wherein the active ingredient imidacloprid is applied after the active ingredient fipronil.

25. A method according to claim 22, wherein the active ingredients imidacloprid and fipronil are applied in the form of two separate agrochemical compositions, each comprising one of the active ingredients and at least one member selected from the group consisting of an agriculturally acceptable solid or liquid carrier and an agriculturally acceptable surfactant, the amount of active ingredients in the compositions thus applied being, in combination, a synergistic arthropodicidally effective amount.

26. A method according to claim 8, wherein the active ingredients imidacloprid and fipronil are applied to the soil.

27. A method according to claim 26, wherein the active ingredients are applied in the seed drill as a granular formulation.

28. A method according to claim 11, wherein the composition is applied to the soil.

29. A method according to claim 28, wherein the composition is applied in the seed drill as a granular formulation.

30. A method according to claim 25, wherein the compositions are applied to the soil.

31. A method according to claim 30, wherein the compositions are applied in the seed drill as granular formulations.

32. A method according to claim 27, wherein the soil is intended for maize or for cereal, and wherein imidacloprid is applied at a rate of between 50 and 500 g/ha and fipronil is applied at a rate of between 50 and 200 g/ha.

33. A method according to claim 29, wherein the soil is intended for maize or for cereal; and wherein the composition is applied at a rate of between 50 and 500 g/ha of imidacloprid and of between 50 and 200 g/ha of fipronil.

34. A method according to claim 31, wherein the soil is intended for maize or cereal, and wherein the compositions are applied at a rate of between 50 and 500 g/ha of imidacloprid and of between 50 and 200 g/ha of fipronil.

35. A method according to claim 8, wherein the plants are protected against wheat bulb flies, seedcorn maggots, Atomaria, centipedes, millipedes, Cicadellidae, aphids, click beetles or wireworms.

36. A plant seed coated with or containing a synergistic arthropodicidally effective amount of imidacloprid and fipronil, the ratio by weight of imidacloprid to fipronil being between 0.02 and 80.

37. A plant seed coated with or containing an agrochemical composition comprising:

(a) a synergistic arthropodicidally effective amount of imidacloprid and fipronil, the ratio by weight of imidacloprid to fipronil being between 0.02 and 80; and (b) at least one member selected from the group consisting of an agriculturally acceptable solid or liquid carrier and an agriculturally acceptable surfactant.

38. A plant seed coated with or containing a mixture of two separate agrochemical compositions, each comprising one of the active ingredients imidacloprid and fipronil and at least one member selected from the group consisting of an agriculturally acceptable solid or liquid carrier and an agriculturally acceptable surfactant, the amount of active ingredients in the mixture being, in combination, a synergistic arthropodicidally effective amount, the ratio by weight of imidacloprid to fipronil being between 0.02 and 80.

* * * * *